(12) United States Patent
Meeder

(10) Patent No.: US 9,854,810 B2
(45) Date of Patent: Jan. 2, 2018

(54) PROCESS TO ELABORATE A BIOSTIMULANT BASED ON SEAWEEDS

(71) Applicant: Patagonia Biotecnología S.A., Santiago (CL)

(72) Inventor: Marcelo Brintrup Meeder, Puerto Varas (CL)

(73) Assignee: Patagonia Biotecnología S.A. (CL)

( * ) Notice: Subject to any disclaimer, the term of this patent is extended or adjusted under 35 U.S.C. 154(b) by 3 days.

(21) Appl. No.: 14/532,422

(22) Filed: Nov. 4, 2014

(65) Prior Publication Data

US 2015/0351408 A1 Dec. 10, 2015

(30) Foreign Application Priority Data

Jun. 4, 2014 (CL) .................................. 1464-2014

(51) Int. Cl.
*A01N 65/03* (2009.01)

(52) U.S. Cl.
CPC .................................... *A01N 65/03* (2013.01)

(58) Field of Classification Search
None
See application file for complete search history.

(56) References Cited

U.S. PATENT DOCUMENTS 7,334,641 B2 * 2/2008 Castellano ............... C09K 8/58
166/246

2003/0104076 A1 * 6/2003 Berkulin ................ A61K 36/28
424/725
2011/0237438 A1 * 9/2011 Marihart ................ A01N 61/00
504/358

FOREIGN PATENT DOCUMENTS

NZ 248783 A * 12/1995

OTHER PUBLICATIONS

Sharma et al., "Biostimulant activity of brown seaweed species from Strangford Lough: compositional analyses of polysaccharides and bioassay of extracts using mung bean (*Vigno mungo* L.) and pak choi (*Brassica rapa chinensis* L.)" J Appl Phycol 24 (2012) 1081-1091.*
Webpage for Whatman qualitative filter paper, Grade 1, Sigma-Aldrich [online] (May 28, 2015) retrieved from URL <http://web.archive.org/web/20150528012321/http://www.sigmaaldrich.com/catalog/product/aldrich/wha10016508?lang=en&region=US>.*
Pise, N. M, and A. B. Sabale. "Effect of Seaweed Concentrates on the Growth and Biochemical Constituents of." Journal of Phytology 2.4 (2010).*

* cited by examiner

*Primary Examiner* — John Pak
*Assistant Examiner* — Daniel L Branson
(74) *Attorney, Agent, or Firm* — Hoffman Warnick LLC

(57) ABSTRACT

Process to elaborate a biostimulant based on seaweeds, comprising acid and alkaline treatment of the algae. The process comprises incorporating American Leonardite and subsequent spraying of product. The invention comprises the composition obtained and its use as germination promoter, root stimulator, among others.

20 Claims, 1 Drawing Sheet

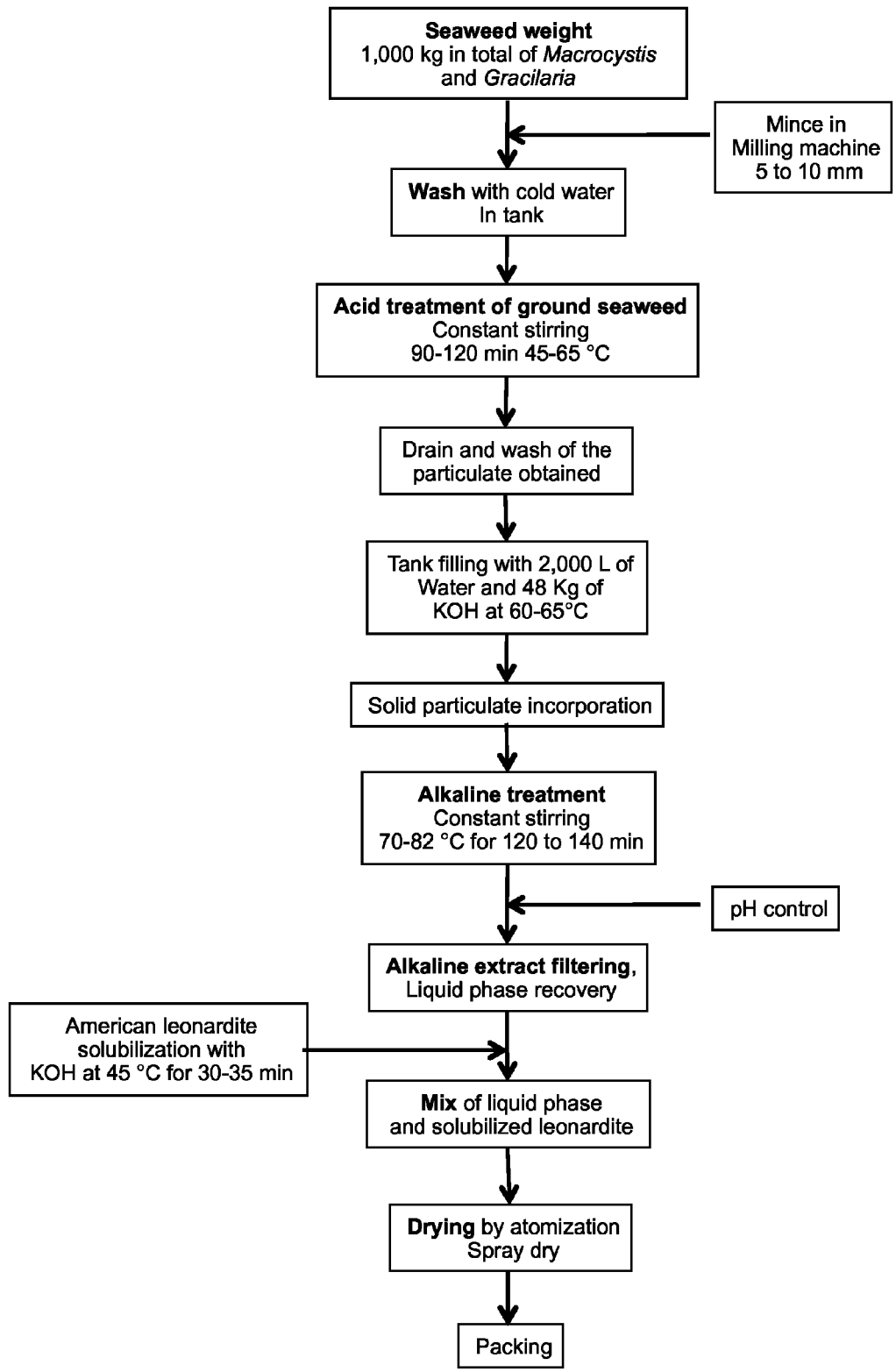

PROCESS TO ELABORATE A BIOSTIMULANT BASED ON SEAWEEDS

CROSS-REFERENCE TO RELATED APPLICATIONS

This application claims the benefit of Chilean Patent Application No. CL 1464-2014, filed 4 Jun. 2014, which is hereby incorporated herein as though fully set forth.

FIELD OF THE INVENTION

The present invention is related to a product based in seaweeds, that is useful to be applied in all types of crops. More specifically, it refers to a biostimulant from seaweeds, that is useful to be applied in all type of vegetal crops, either agricultural or forest, with the purpose to avoid chemical fertilizers that are polluting or harmful to human health and to the environment.

BACKGROUND

Currently there is a wide range of methodologies to obtain seaweed-based fertilizers.

The pending patent request WO2013/108188 describes a method to obtain fertilizers. The method the application of high pressures to seaweeds to release its intracellular content. This extract is complemented with zeolite and meat and bone meal (MBM). The application does not claim the product in its current commercial form, i.e. pellet or grind down. This document is part of the state of the art.

Patent EP1534757 claims a process to obtain a fertilizer and phycocolloids in parallel. The extraction of the fertilizer includes washing the seaweeds; blend the seaweed through milling; filtering and recovery of the liquid phase; addition of a certain preservative; concentration through evaporation or by the use of membranes. The method does not mention acid and/or base treatment, and for that reason the incorporation of a preservative is probably required. This patent is part of the state of the art.

Patent CL 47236 from the Universidad de los Lagos claims a method that includes the use of HCl as the acidifying agent and $K_2CO_3$ as the alkalizing agent for the treatment of the seaweeds *Macrocystis pyrifera* and *Ulva rigida*, obtaining a liquid final product (Makromix).

Comparatively, the product of the present invention is superior to other products obtained by comparable procedures, because of the particularity of the process and the raw material used, allow to achieve a higher bioavailability of the nutrients contained in the seaweeds and this is traduced in better yields, both in the modalities of foliar (soil) application as in the phase of seed germination.

In the quest of better field results, the present invention differs in key aspects from the process that delivers a superior product, like the use of a different pool of seaweeds, the use of acetic acid and KOH, that finally result in higher process yield and quality of the final product.

DESCRIPTION OF THE INVENTION

Because of the growing demand on products that are organic, environmentally friendly and harmless to human health, the need for natural biostimulants has been raised, that are similar or more effective that the traditional stimulants used. The present invention discloses a biostimulant that is capable to increase the growth rates and yields of a wide range of crops.

In order to efficiently obtain the product, with a better performance to that described in the state of the art, the present invention claims a method for the preparation of a natural vegetal biostimulant, that includes the treatments of seaweeds with acetic acid as acidifying agent, and KOH as alkalizing agent. The present invention also includes the use of american leonardite, to finally obtain a dry product, that is easy to use, transport and store.

The present invention claims a method that takes advantage in the availability of seaweeds of low commercial price as raw material to produce a biostimulant, that is useful to be applied on seeds, aerial parts of the plants or soil. To accomplish this, red and brown algae from the *Macrocystis* and *Gracilaria* genera have been selected, like, for example, *M. pyrifera* and *G. chilensys*, respectively.

Red and brown algae contain high concentrations of vegetal hormones or phytohormones, free amino acids and oligosaccharides. The composition claimed, due to the utilization of these seaweeds and the innovative method of elaboration, extracts and preserves, and in consequence provides to the vegetal or seed treated high concentrations of three phytohormones: auxins, cytokinins and gibberellins, that are required for the optimal development of plants.

Furthermore, 17 amino acids present in seaweeds that are necessary for protein synthesis (alanine, arginine, aspartic acid, cysteine, glycine, glutamic acid, histidine, isoleucine, leucine, lysine, methionine, phenylalanine, proline, serine, threonine, tyrosine and valine) ensure a better development of the plants. In normal conditions plants produce their own amino acids, but in stress conditions photosynthesis is reduced and in consequence its metabolism is slowed down. The product from this patent, delivers exogenously these amino acids and reduces the stress in plants, increasing the absorption of nutrients and improving its translocation and the permeability of the cell membranes.

In addition, oligosaccharides (laminaran, manitol) activate the function of phytoalexins in cultivated plants, resulting in a higher vigor and resistance of the plant to diseases and plagues, optimizing the technical use of them.

In sum, the method claimed allows the extraction of nutrients contained in seaweeds foliage, without degradation nor requiring the reincorporation of those nutrients from external sources.

Finally, the present invention provides a great amount of organic matter, that is beneficial to improve the soil treated, by means of humic and fulvic acids incorporation that come from leonardite, that is a fossil mineral that is found together with lignite and that is the main source of these acids. This solid, concentrated and humidified organic matter, contain humic substances, that help to improve the soils both in a physical-chemical and biological manner. It can be applied together with solid and liquid fertilizers to obtain a better performance. Is an intermediate material, between turf and lignite, and is derived from the transformations (diagenesis) of vegetal remains, buried at approximately 10 meters, when together with water percolation from rain and the presence of atmospheric oxygen, led to a progressive enrichment of the humic substances.

It is possible that brown lignite may be confused with leonardite, even that they have clear differences: lignite suffers a carbonization process, whereas leonardite does not, and at the same time, leonardite has a high oxygen content and lignite loses almost all of it, and finally, leonardite has an open structure, and lignite comprises, because of the pressure suffered during its burial.

Main Functions of Leonardite:

Acts as a soil corrective, achieving the rehabilitation of soils by providing them a fluffy structure, reducing compression and favoring ventilation and porosity of soil; it helps to water retention; it favors root growth; it reduces the need of mineral fertilizers; it improves the quality and size of crops; it accelerates the plant's vegetative cycle; it improves the soil physical-chemical properties; it improves the soil salinity; it has a high power to chelate cations.

FIGURE DESCRIPTION

FIG. 1: Flowchart that exemplifies the complete process for biostimulant extraction.

DETAILED DESCRIPTION OF THE INVENTION

In the following pages the physical-chemical fundaments are described for each of the steps of the process and the evidence that show the optimal results as well as the detailed procedure to reproduce those results with the available resources.

Seaweed Milling

Seaweed milling has as primary aim to facilitate the use of them during storage, salt removal or washout and the acid treatment. Another benefit derived from milling is to reach a particle size that allows to reagents uniformly penetrate to the seaweed, resulting in more homogenous reactions and so it gives better monitoring of chemical treatments. The use of this maneuver will result in obtaining fragments, that make possible to perform in a satisfactory way the subsequent treatments. This is done using a grinder. With this mechanism a more uniform particle size is obtained resulting in more mass fluidity during seaweed's chemical treatments. The preferred particle size ranges between 5 and 10 mm.

For processing in the factory, 1000 kg of fresh seaweed are used, they are deposited in a 5000 L capacity vat (tank). If seaweeds will not be immediately processed, they can be stored for 24 hours without freshwater.

Seaweeds are employed in a ratio of *Macrocystis: Gracilaria* from between 70:30 to 95:5 respectively.

Salt Removal or Washout

This step consists in washing the seaweeds with water, in order to eliminate and remove mineral salts, seawater excess, sand, small mollusks, etc. The process is carried out with water at room temperature for until 60 min.

Acid Treatment of Seaweeds

The acid treatment step has two basic functions. First it is done to remove the soluble mineral salts and organic matter in excess, that was not removed by the previous wash, as well as the sediments and organisms associated to seaweeds. Second, is to perform an ion-exchange chemical reaction mainly between calcium ions and other divalent cations, like magnesium and strontium, that are contained in seaweeds as divalent metal alginates, and originating alginic acid (HAlg).

Although there is currently in the state of the art a process that employs HCl, we have discovered that the use acetic acid results in superior acid treatment. Both HCl and acetic acid run in a similar way in the chelate fixation that is required in the acid process. However, acetic acid is accepted in the organic process without HCl limitations, such as its low boiling point, that implies a higher acid loose at the temperature in which the acid treatment is done, with respect to acetic acid. Additionally, HCl treatment only tolerates a 1.5% of the acid, an amount that is not enough for an efficient chelate fixation in a short time of reaction.

1. The Reaction Carried Out is the Following:

Physically, this is a heterogeneous reaction between solid seaweed particles and the acid solution.

2. Liquid/Solid (L/S) Relation.

The ratio of water respect to the volume of processed seaweeds has two purposes; first, is to provide fluidity to the mass in order to obtain an homogeneous reaction, second is to remove the mineral salts and solids associated to seaweed particles.

a) Factors Implied in Mass Fluidity.

Mass fluidity depends not only in the liquid amount but also in the particle size. The smaller the size of the particle the lesser the amount of water required. However, the minimal size of the particle is limited by two important factors:

Viscous nature of seaweeds: Naturally, fresh seaweed have a viscous texture, which is incremented after fractioning by the release of fucoidins in the cutting edges.

Separation of liquid:solid phases: Very small particles are not convenient because of the complications in the mechanisms to separate solids and because of the increased loss of small particles In conclusion, a particle size between 5 to 10 mm present an homogeneous fluidity with a minimal liquid solid relationship of 2:1.

b) Removal of Mineral Salts and Soluble Organic Matter.

Humid seaweeds contain an 8-10% of mineral salts and soluble material. These impurities often causes interferences in some of the steps of the process of preparation of the biostimulant, so it is necessary to reduce them at the beginning of the process. A 1.5-3.0% reduction avoid significant interferences in subsequent reactions. In previous experiences, the process for salt removal was standardized to 1.0-3.0% levels, applied a 30 minutes wash in a liquid:solid relation of 2:1. With this washing system the water consumption is optimized and an efficient reduction in salt content is achieved.

3. Acid Consumption.

During the acid wash of seaweeds a ion-exchange reactions occurs between de divalent metal salts from alginic acid that is contained in seaweeds ($Ca^{2+}$, $Mg^{2+}$, $Sr^{2+}$) and proton $H^+$. This treatment is done in order to transform all the alginate salts contained in the seaweed to its generic form of alginic acid.

Depending on the alginate content in the seaweed, this reaction consumes an amount of acid close to the stoichiometric relationship.

In practice, the total expense of acid, including the lost in residues should be the closest to said relationship. This will be depend on the efficiency of the wash mechanism.

The washing system suggested for salt removal was used to optimize acid consumption.

The average expense recorded is between 55 and 65 L of acetic acid, more preferentially between 58 and 62 L of acetic acid for 1,000 kg of fresh seaweed.

4. Time and Temperature of Reaction.

Time and temperature notably influence a reaction's kinetics. These parameters determine the viscosity of the final product due to the susceptibility of alginic acid to break down at high temperatures or prolonged exposures to acid.

The reaction time is from 90 to 120 minutes at a temperature of 45-65° C., time that is satisfactory to complete the reaction y there is no alginate degradation, protecting the compounds from seaweeds, and obtaining a chelated base.

The parameters previously mentioned are resumed in Table 1:

| | |
|---|---|
| liquid/solid relationship | 2:1 |
| Amount of acetic acid | 55 to 65 L |
| Total time of residency | 90-120 min |
| Temperature of reaction | 45-65° C. |
| Wash | 30 min |
| Batch Size | 1,000 kg of fresh seaweeds |

Once the acid treatment is finished, the mixture is filtered with sieve, recovering the solid particulate, that will be subject to digestion or alkaline treatment.

Digestion and Extraction (Alkaline Treatment)

During digestion and extraction a neutralization reaction occurs between alginic acid contained in algae particles and a potassium alkali, producing in this case a potassium alginate en aqueous solution. The reaction carried out is the following:

$$HAlg + KOH \longrightarrow KAlg + H_2O$$

This reaction is one of the most delicate of the process, because a big proportion of the performance and the quality of the final product depends on the adequate control of the physical-chemical parameters that affects it.

Physically, this is a heterogeneous reaction between the solid particles from the acid pretreated seaweed and the alkaline solution. The alkali penetrates in the algae particle, converting the insoluble alginic acid in soluble sodium or potassium alginate in aqueous media, finally resulting in a very viscous solution with millimetric insoluble cellulose filaments. The total dissolution of the particles determine the maximal yield of the raw material.

Basically the reaction is completed at a pH higher than 7, preferentially 8.5 to 14, in a reaction time that can range from 120 to 150 min depending on the following factors:

a) Temperature. The temperature is one of the most important factors in the reaction due to its control in the reaction's kinetics and the viscosity of the final product. The range in which the viscosity can be controlled varies from 70 to 82° C.

b) Particle size: A particle's size <10 mm gives very good results with the appropriate combination of the other parameters.

c) liquid:solid relationship and stir. During digestion is recommended to have a fluidity that allows to homogeneously stir the suspension using minimal water.

A 2:1 liquid:solid relationship respect to fresh seaweeds results in a viscosity that allows a homogenous stir of the suspension and gives enough aqueous media to dilute the extract.

d) pH. In the process described optimal results were obtained using a pH range between 8.5 and 14 (given by the use of potassium hydroxide). Under these conditions maximal yields between 3.5 and 3.8% of potassium alginate were obtained, that are the base of the alkaline extract used as biostimulant from fresh seaweeds. The alkali consumption is between 45 and 50 kg of potassium hydroxide per initial ton of fresh seaweed.

The parameters previously mentioned are resumed in Table 2:

| | |
|---|---|
| Temperature | 70-82° C. |
| pH | 8.5-14 |
| Time | 120-150 min |
| liquid/solid relationship | 2:1 |
| % of KOH respect to fresh seaweeds | 3 to 6% |

The digestion is carried out as follows:

Potassium hydroxide is dissolved in water at 60-65° C. and milled seaweeds or the solid particulate recovered from the acid treatment are added, then the mixture is stirred for 120 to 150 min at 70-82° C. pH is adjusted with potassium hydroxide. The final product of this reaction is a viscous solution (400-600 Cps) of potassium alginate with millimetric cellulose residues.

The end of the hydrolysis step is initiated lowering the temperature of the mixture, followed by the filtration of the alkaline extract.

5. Filtration

The aim of filtration is to clarify the solution of the alkaline extract, removing the cellulose insoluble particles that remains from digestion step. The monitored parameters in this stage are the filtrate purity and filtrate velocity, which depends on the filtration media used. Preferentially the filtration of the solution is carried out with a primary and a secondary filter with a final net size of 50, without excluding another compatible methods.

6. Leonardite Processing

Leonardite is subjected to an activation process through chemical hydrolysis to separate it in humic and fulvic acids (active components) and other non hydrolysable components (clays and humines). This helps to extract all the nutrient capacity of leonardite in short time, process that in a natural manner will take several years.

Digestion is done in aqueous media, with KOH and controlled temperature. For each 100 kg of leonardite 500 L of water at 40-45° C. are used, and between 47 and 53 kg, more preferentially between 50 and 51 kg of KOH. The mixture is stirred at 45-50° C. for 30 to 40 min.

Once the digestion of leonardite is finished, it is mixed with the alkaline extract from seaweed, recovered from the alkaline treatment, in a concentration that ranges from 5 to 20% v/v.

7. Drying

The process consists in pulverize the fluid inside a chamber subjected to a controlled stream of hot air. This fluid is atomized in millions of individual microdrops by a rotating disc or a spray nozzle. By this process the area of contact of the pulverized product is enormously augmented and inside the chamber the hot air stream induces the rapid vaporization of water in the center of each microdrop were the solid is located, resulting in a smooth dry without a big thermal shock, transforming the product in powder and finishing the process with the collection of this powder.

The final product is a fine powder, resulting from the drying of the mixture from the extract from processed seaweeds and the solubilized american leonardite. This presentation facilitates transportation, storage and preservation, keeping the biological properties of the product.

For application on ground, the product is simply dissolved in water, reconstituting the extract (28 gr×L) depending on the requirements, being able to be applied by irrigation or spray.

The product has been stored under these conditions for periods longer than 3 years, keeping the biostimulant properties of the product, a feature that is favored for its powder presentation format and its low hygroscopy.

EXAMPLES

Monitoring of a Consignment in the Factory

The following is a description of a typical operational process in the factory including the monitoring that is performed in every step of the process starting with a base of a 1,000 kg consignment of fresh seaweeds.

Preparation of a Consignment

Seaweeds must be fresh. At the beginning of the process the following preparations must be done:

2,000 L of water with 61 L of acetic acid are prepared in the acid wash tank.

2,000 L of water are stored in the digestion tank.

Reagents are heated to a temperature close to 45-50° C. and the acid wash can now begin.

Procedure of the Operation

1. Collect 900 kg of *Macrocystis pyrifera* and 100 kg of *Gracilaria chilensis*.
2. Fraction them to a size between 5 to 10 mm in the milling machine, wash and weight 1,000 kg;
3. Incorporate 2,000 L of water and 61 L of acetic acid at 45-65° C. with constant stirring for 100 min. Once finished, the liquid phase is eliminated and it is washed with water.
4. 2,000 L of water are added, and the temperature is set to 60° C.; 48 kg of potassium hydroxide are dissolved and milled seaweeds are added. Temperature is raised to 79° C. under constant stirring for 2 hours. pH is adjusted at 8.65 and the mixture is cooled down.
5. Filtration. Once the residual particles have sedimented, a filtration takes place, eliminating the particulate; american leonardite is incorporated, hydrolized at 10% v/v.
6. Adjust pH to 7, if required, with phosphoric acid, acetic acid or other suitable acids.
7. Dry until obtain the powder.
6. Leonardite Processing For obtaining humic and fulvic acids.

500 L of water at 45° C. are employed. The mixture is stirred until the end of the process. 50 kg of KOH and 100 kg of american leonardite are added. Temperature is hold at 45° C. for 30 to 35 minutes, until the initial product is completely dissolved.

Example 1: Comparative Assay in Wheat

| Variety | Pandora INIA |
|---|---|
| Seed dose | 220 kg × Ha |
| Total area | 18 ha |
| Bioestimulant application area | 1 ha |
| Makromix application area | 1 ha |
| Control area | 16 ha |

Treatment was applied to seeds pre-sowing and then to the plant in the end of culm state.

SCHEDULE OF APPLICATIONS

| Date/period | Product | Dose | Watering | Area |
|---|---|---|---|---|
| 15-Jul/Pre-sowing | Biostimulant | 0.5 L × 100 kg of seed | 1 L × 100 kg | 1 ha |
| 15-Jul/Pre-sowing | Makromix | 0.5 L × 100 kg of seed | 1 L × 100 kg | 1 ha |
| 25-Oct/End of culm | Biostimulant | 3 L × ha | 66 L × ha | 16 ha |
| 25-Oct/End of culm | Makromix | 3 L × ha | 66 L × ha | 16 ha |

Both treatments showed differences respect to control, in the measures of root growth, vegetative development and plat height, evidencing notorious differences in harvest yield and the milling quality.

MEASUREMENTS

| 05-Nov | Biostimulant | Makromix | Control |
|---|---|---|---|
| Root growth | 15 | 14.5 | 14 |
| Roots lenght m/m | 40 | 38 | 38 |
| Plant weight Grs. | 91 | 78 | 68 |

HARVEST

| 15-Feb | Biostimulant | Makromix | Control |
|---|---|---|---|
| qq × ha. | 71.3 | 66.23 | 60.46 |

CALIDAD MOLINERA

| 20-Feb | Biostimulant | Makromix | Control |
|---|---|---|---|
| Hectoliter weight kg/HL | 85.3 | 85.3 | 84.6 |
| Dry gluten kg/HL | 11.93 | 10.4 | 9.9 |

Example 2: Comparative Assay in Raspberry

In raspberry crop, Meeker variety, the following assay was performed in a total area of 1.98 ha:

| Bioestimulant application area | 0.92 ha |
|---|---|
| Makromix application area | 0.94 ha |
| Control area | 0.12 ha |

Four applications of each fertilizer were done, at a rate of 6.5 L per ha, in a period of 80 days. In both applications a higher development of buds and shoots as well as an apparent increase in vigor, additionally a higher need of fertilization is observed, mostly nitrogen after each application, a fact that is probably explained by the increase in the plant's rate of biomass development.

The yield in kg of pulp per hectare was evaluated. Yield of each treatment according to quality and expressed in kg/ha.

| Classification According quality | Biostimulant | Makromix | Control |
|---|---|---|---|
| IQF > 18 | 2,777.75 | 2,509.66 | 2,430.48 |
| IQF < 18 | 1,860.38 | 1,869.00 | 1,789.37 |
| Pulp | 486.875 | 438.347 | 463.1487 |
| Total yield | 5,125 | 4,817 | 4,683 |

Example 3: Comparative Assay in *Eucalyptus*

A seed from Puacho 3 (Anchile) was employed, subjected to 3 days of soaking in water and 30 seconds of soaking in Sodium hypochlorite, 21 days of cold and 3 days in chamber. Pine bark from Madexpo and 3 kg of NPK (3-33-3) was used as substrate.

30 seed trays with 96 cavities each were used. A solution of 1% of Biostimulant and Makromix was applied. A second application was performed at a concentration of 0.5%.

Procedure:

Two treatments plus the control (Ultrasol) were done, each one with 5 replicas. Sowing was carried out using an automatic sow seed machine. After that a solution with 1% fertilizer was applied with a watering can. Then, trays were taken to the germination chamber at a fixed temperature of 27° C. for 3 days.

Once initiated germination, trays were taken to a farm building with temperatures ranging between 20 and 30° C. during day and 4 and 15° C. during night. Watering, depending on weather conditions, was done twice a day.

The controlled variables controlled were the germination percentage, root collar diameter (RCD) and average height after 10 days of sow.

Second application was done with 0.5% dilution in 1,500 cc of water. After 36 days of sow, a second control of germination was done.

Results were the following:

| Fertilizer | % Germination | | Average height | |
|---|---|---|---|---|
| | 1st measurement | 2nd measurement | 1st measurement | 2nd measurement |
| Biostimulant | 77.5 | 77.08 | 1.08 | 2.74 |
| Makromix | 59.79 | 58.54 | 1.02 | 2.12 |
| Ultrasol | 76.88 | 75.83 | 1.04 | 2.70 |

Example 4: Comparative Assay in Grape

| Variety | Red Globe |
|---|---|
| Location | Copiapó-Chile |
| Cultivated field | 8 years |
| Total area | 5 ha |
| Biostimulant applied area | 2 ha |
| Makromix applied area | 2 ha |
| Control area | 1 ha |

The following application protocol was employed for both products:

| Application period | Dose | Watering |
|---|---|---|
| 40 cm bud | 3 L × ha | 1.6 L × ha |
| Curdle | 3 L × ha | 1.6 L × ha |
| Bunch closure | 3 L × ha | 1.6 L × ha |
| Veraison | 3 L × ha | 1.6 L × ha |

Parameters were measured 15 days pre-harvest and during harvest.

| measurement 15 days pre-harvest | | | |
|---|---|---|---|
| | Biostimulant | Makromix | Control |
| Bunch weight | 506 | 490 | 456 |
| Equatorial diameter | 19.5 | 19.2 | 19 |
| Brix degrees | 18.6 | 18.4 | 18.3 |
| Harvest | | | |

| measurement 15 days pre-harvest | | | |
|---|---|---|---|
| | Biostimulant | Makromix | Control |
| Bunch weight | 694 | 642 | 636 |
| Equatorial diameter | 23.8 | 22.1 | 21.96 |
| Polar diameter | 2.8 | 2.7 | 2.7 |
| Brix degrees | 19.35 | 19.1 | 19 |

It is evident the differences between treatments and control, in all the parameters measured, being the treatment with Biostimulant notoriously superior with respect to Makromix and Control.

Example 5: Comparative Assay in Tomato

| Variety | Titan |
|---|---|
| Total Area | 0.6 ha |
| Biostimulant Area | 0.3 ha |
| Makromix Area | 0.3 ha |
| Layout of plantation | 1.2 m between row y 0.2 over row |
| Watering | Drip irrigation with tape. 4 L × m linear |
| Applications | 8 foliar applications with 400 L × ha |
| Dose | 2 L × ha in C7 |

Eight applications of each treatment were done, every 20 days. In the 2 first applications no differences were observed in plant development, however, starting the third application the vigor of the Biostimulant-treated seedlings was increased, resulting in a notorious increase in total yield and in a better fruit quality at harvest.

| HARVEST Kg × ha | | |
|---|---|---|
| Quality | Bioestimulant | Makromix |
| Tomato 1$^{st}$ | 175,109 | 117,600 |
| Tomato 2$^{nd}$ | 50,031 | 39,210 |
| Tomato 3$^{rd}$ | 25,015 | 39,190 |
| Total | 250,155 | 196,000 |

What is claimed is:

1. A method of producing a biostimulant from seaweed, the method comprising:
   a) milling fresh seaweed;
   b) washing the fresh seaweed;
   c) treating the washed seaweed with an acid;
   d) treating the product of c) with KOH;

e) separating and recovering the liquid phase of the product of d);
f) adding hydrolized American leonardite to the liquid phase; and
g) drying the product of f) to obtain a powder.

2. The method of claim 1, wherein the seaweed is selected from a group consisting of *Macrocystis* spp. and *Gracilaria* spp.

3. The method of claim 1, further comprising:
milling the seaweed to a particle size of between about 5 mm and about 10 mm.

4. The method of claim 1, wherein washing the seaweed is carried out with water at room temperature.

5. The method of claim 1, wherein the acid includes acetic acid.

6. The method of claim 5, wherein the acetic acid is employed at a ratio of between 55 L and 65 L per 1,000 kg of seaweed.

7. The method of claim 1, wherein treating the washed seaweed with an acid is carried out at between 45° C. and 65° C. for between 90 minutes and 120 minutes.

8. The method of claim 1, wherein treating the product of c) with KOH employs KOH at a ratio of between 45 kg and 50 kg per 1,000 kg of seaweed.

9. The method of claim 1, wherein treating the product of c) with KOH is carried out at between 70° C. and 82° C. for between 120 minutes and 150 minutes.

10. The method of claim 1, wherein treating the product of c) with KOH is carried out at a pH between about 8.5 and about 14.

11. The method of claim 1, wherein treating the product of c) with KOH includes cooling the product of c).

12. The method of claim 1, wherein adding hydrolized American leonardite includes adding hydrolized American leonardite at a range between 5% and 20% v/v.

13. The method of claim 1, wherein the hydrolized American leonardite is hydrolyzed by alkaline treatment with between 47 kg and 53 kg of KOH per each 1,000 kg of American leonardite at between 40° C. and 50° C. for between 30 minutes and 40 minutes with constant stirring.

14. The method of claim 1, wherein drying the product of f) includes spray drying.

15. The method of claim 1, wherein treating the washed seaweed with an acid produces alginic acid.

16. The method of claim 15, wherein treating the product of c) with KOH produces potassium alginate.

17. A biostimulant composition prepared according to the method of claim 1.

18. The biostimulant composition of claim 17, wherein the composition is suitable for storage for at least three years in the form of a dry powder.

19. The method of claim 1, further comprising:
h) rehydrating the powder of g).

20. A rehydrated biostimulant composition prepared according to the method of claim 19.

* * * * *